United States Patent
Taulu

(10) Patent No.: US 7,502,720 B2
(45) Date of Patent: Mar. 10, 2009

(54) METHOD AND DEVICE FOR USING A MULTI-CHANNEL MEASUREMENT SIGNAL IN SOURCE MODELLING

(75) Inventor: Samu Taulu, Helsinki (FI)

(73) Assignee: Elekta AB (publ) (SE)

( * ) Notice: Subject to any disclaimer, the term of this patent is extended or adjusted under 35 U.S.C. 154(b) by 0 days.

(21) Appl. No.: 10/572,570

(22) PCT Filed: Sep. 14, 2004

(86) PCT No.: PCT/FI2004/000532

§ 371 (c)(1),
(2), (4) Date: Jan. 3, 2007

(87) PCT Pub. No.: WO2005/030051

PCT Pub. Date: Apr. 7, 2005

(65) Prior Publication Data

US 2007/0108962 A1     May 17, 2007

(30) Foreign Application Priority Data

Sep. 26, 2003    (FI) ................................. 20031394

(51) Int. Cl.
*G06F 15/00* (2006.01)
*H04B 15/00* (2006.01)
*A61B 5/05* (2006.01)

(52) U.S. Cl. ................ 702/189; 702/198; 600/409; 324/247

(58) Field of Classification Search .......... 702/189, 702/198; 600/409; 324/247
See application file for complete search history.

(56) References Cited

U.S. PATENT DOCUMENTS 4,736,751 A * 4/1988 Gevins et al. ............... 600/545
4,977,896 A * 12/1990 Robinson et al. ........... 600/409

(Continued)

FOREIGN PATENT DOCUMENTS

EP     0 632 353 A1     1/1995

(Continued)

OTHER PUBLICATIONS

"Multipole expansions of electromagnetic fields using Debye potentials", C. G. Gray, American Journal of Physics, vol. 46, pp. 169-179, 1978.

*Primary Examiner*—Eliseo Ramos Feliciano
*Assistant Examiner*—Janet L Suglo
(74) *Attorney, Agent, or Firm*—Studebaker & Brackett PC; Donald R. Studebaker

(57) ABSTRACT

A method for interpreting the current distribution of an object being measured using basis vector components calculated from the measured signals. The components in question have been so selected that they describe the features, as independent as possible, of the current distribution being examined, which enhances the computation and makes it more accurate. This is achieved by converting the measured signals into a more natural form from the standpoint of the current distribution while totally eliminating the signals associated with the external interferences. After the conversion, the source modeling is performed in an optimal manner using the basis vector components of the signal space instead of the actual measurement signals. One substantial feature of the invention is that after the conversion, the source model need not be regularized any more.

17 Claims, 1 Drawing Sheet

U.S. PATENT DOCUMENTS

Figure 1:
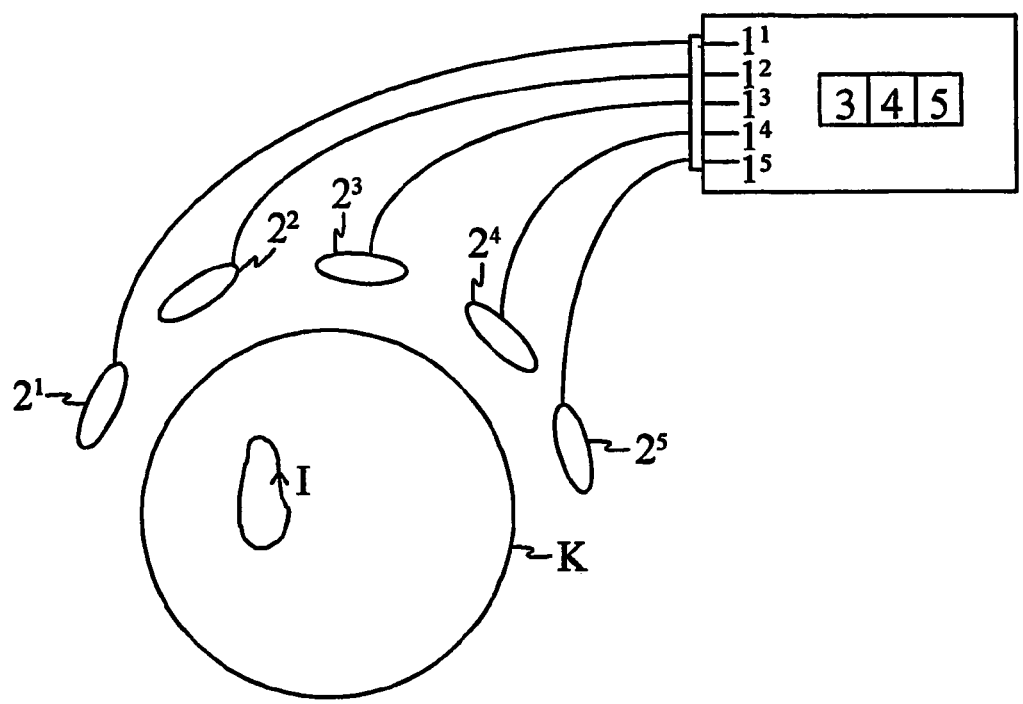

| | | | |
|---|---|---|---|
| 5,269,325 A | | 12/1993 | Robinson et al. |
| 5,644,229 A | * | 7/1997 | Dossel et al. ............... 324/247 |
| 5,671,740 A | * | 9/1997 | Tomita et al. ............... 324/263 |
| 5,687,724 A | * | 11/1997 | Jewett et al. ............... 600/409 |
| 6,370,414 B1 | | 4/2002 | Robinson |
| 6,374,131 B1 | | 4/2002 | Tomita et al. |
| 6,454,036 B1 | * | 9/2002 | Airey et al. ............... 180/167 |

FOREIGN PATENT DOCUMENTS

| | | |
|---|---|---|
| EP | 0 982 597 A2 | 3/2000 |
| EP | 1 302 160 A1 | 4/2003 |

* cited by examiner

METHOD AND DEVICE FOR USING A MULTI-CHANNEL MEASUREMENT SIGNAL IN SOURCE MODELLING

FIELD OF THE INVENTION

The present invention relates to a new and advanced method for using a multi-channel measurement signal in source modeling. In particular, the present invention relates to a new way of converting the measurement signals measured using a multi-channel measuring device that measures an irrotational and sourceless vector field into a form optimal from the standpoint of the source modeling.

BACKGROUND OF THE MENTION

The electrical operation of an object to be examined can be examined e.g. by measuring the magnetic field produced by the electric currents of the object using sensors placed outside the object. The modeling of a source distribution thus obtained based on the measured signals is, however, very difficult because each magnetic field distribution can be produced by many different source distributions. In other words, a source distribution cannot be solved unambiguously based on the measured signals, so to solve the problem, different restrictive conditions must be set, such as some parametric model based on prior information for a current, or a non-parametrised norm restriction.

For the non-parametrised modeling of a continuous current distribution, minimum norm estimates are usually used, in which there is an attempt to explain a signal measured using a multi-channel measurement device with a current distribution whose norm is as small as possible. As the norm, usually an L1 or L2 norm is selected, of which the previous is the sum of the lengths of the current elements over the selected volume, and the latter is the sum of the squares of the lengths of the current elements over the selected volume. The calculation of the minimum norm estimates has been described e.g. in publications "Interpreting magnetic fields of the brain: minimum norm estimates", M. S. Hämäläinen et al, Medical & Biological Engineering & Computing, Vol. 32, pp. 35-42, 1994, as well as "Visualization of magnetoencephalographic data using minimum current estimates", Uutela K. et al, NeuroImage, Vol. 10, pp. 173-180, 1999.

Conventional minimum norm estimates involve inherent problems such as slowness of calculation and susceptibility to noise. For example, in the case of an L2 norm, one needs an inverse matrix of matrix G, whose element (i, j) contains the inner product of the lead fields of the ith and jth measurement sensor, so one must calculate these inner products for each pair of sensors. The lead field is so determined that the signal measured by a sensor is the projection of the current distribution for the lead field of the sensor in question. The noise problems are due to the fact that matrix G calculated for the sensors is susceptible to noise, so in the calculation of its inverse matrix, regularisation is needed in the practical situations.

Regularisation methods, such as the truncation regularisation of the singular value decomposition, usually are non-intuitive, and usually also to be solved for each case specifically. A regularisation of the wrong type may lead to an erroneous modeling result.

Therefore, source modeling nowadays still involve problems such as the difficulty and slowness of the computation, the possible errors caused by noise, as well as the case-specificity due to the regularisation. Further, as stated above, the regularisation may cause considerable errors to the final computation result.

OBJECTIVE OF THE INVENTION

The objective of the invention is to eliminate the drawbacks referred to above, or at least significantly to alleviate them. One specific objective of the invention is to disclose a new type of method which can be used to considerably lighten and accelerate the computation associated with the modeling of a continuous current distribution, as well as to lessen the problems with noise.

As for the features characteristic of the invention, reference is made to them in the claims.

DESCRIPTION OF THE INVENTION

The present invention relates to a new kind of manner of determining the continuous current distribution of an object being examined using-basis vector components of signal space calculated from the measured signals. The components in question have been so selected that they describe the features, as independent as possible, of the current distribution being examined, which enhances the computation and makes it more accurate.

The basic idea of the invention is that because the computation of the inner products of the sensor fields is hard and difficult using a conventional set of sensors, it is worth using a special set of sensors, whose lead fields are orthogonal and, if possible, to be analytically computed. In principle, this can be implemented by a suitable physical set of sensors. As a suitable physical set of sensors is, however, often quite difficult to manufacture, it is, in most of the cases, advantageous to use virtual sensors computationally generated from a conventional set of sensors, i.e. the measurement signals are converted into other ones by a suitable conversion so that they correspond to the signals that the virtual measurement device would have measured. At the same time, it is possible, if necessary, to eliminate the signals associated with external interference. This conversion has been described e.g. in patent application FI20030392, which is incorporated herein by reference. After the conversion, the source modeling is performed in an optimal manner using the basis vector components of the signal space instead of the actual measurement signals. One substantial feature of the invention is that after the conversion, the source model need not be any more regularised.

Thus, the present invention relates to a method for determining the current distribution of an object by measuring the magnetic fields in the vicinity of the object using a multi-channel measurement device. Advantageously, at least one measurement sensor corresponds to each channel, and the object is approximated by a spherical-symmetrical conductor. The object can be e.g. a human being's head.

According to the invention, a multi-channel measurement signal corresponding to each measurement sensor is converted into the signals of a predetermined set of virtual sensors, and the current distribution of the object being examined is determined by depth r from the signals of the set of virtual sensors in a beforehand selected orthonormal function basis. In that case, the estimation of a current distribution is fast and robust. Further, to achieve the set of signals corresponding to the set of virtual sensors, a multi-pole development is calculated from a multi-channel measurement signal. A multi-pole development can be calculated in two ways: by taking into account the magnetic fields emitted by sources outside the object being measured, or by ignoring them.

Advantageously, as the orthonormal function basis, a basis with the following form is selected:

$$\vec{J}(\vec{r}) = \sum_{l=0}^{L} \sum_{m=-l}^{l} c_{lm} f_l(r) \vec{X}lm(\theta, \varphi),$$

wherein $f_l(r)$ is a radial function to be freely selected and $\vec{X}_{lm}(\theta,\phi)$ is so-called vector spherical harmonic. In that case, it is possible to place the function basis into a current distribution equation, and the coefficients of the current distribution are analytically solved based on the equation:

$$c_{lm} = \hat{\gamma}_l M_{lm} \left[ \int_0^R r^{l+2} f_l(r) dr \right]^{-1},$$

wherein $\hat{\gamma}_l$ is a constant associated with order l and R is the radius of the sphere to be examined. Advantageously, function $f_l(r)$ is used to adjust the depth weighing of a current distribution model.

Furthermore, the invention relates to a measurement device for determining the current distribution by measuring magnetic fields in the vicinity of the object. The measurement device includes a set of measurement channels that measure an irrotational and sourceless vector field, whereby at least one measurement sensor corresponds to each channel, and processing means for processing the measurement signal. Advantageously, the object is approximated with a spherical-symmetrical conductor.

According to the invention, the processing means include a conversion module for converting a multi-channel measurement signal corresponding to each measurement sensor into the signal of a predetermined set of virtual sensors; and calculation means for determining the current distribution of an object being examined or for calculating by depth r from the signals of the set of virtual sensors in a beforehand selected orthonormal function basis. In one embodiment, the calculation means are arranged to calculate a multi-pole expansion from a multi-channel measurement signal.

The invention enables one to considerably lighten and accelerate the calculation associated with the modeling of a continuous current distribution. The invention further enables one to reduce the problems associated with noise. Further, the invention simplifies the regularisation of a source model, or eliminates the need for it, thus also significantly reducing the possibility of error.

LIST OF FIGURES

Figure 2:
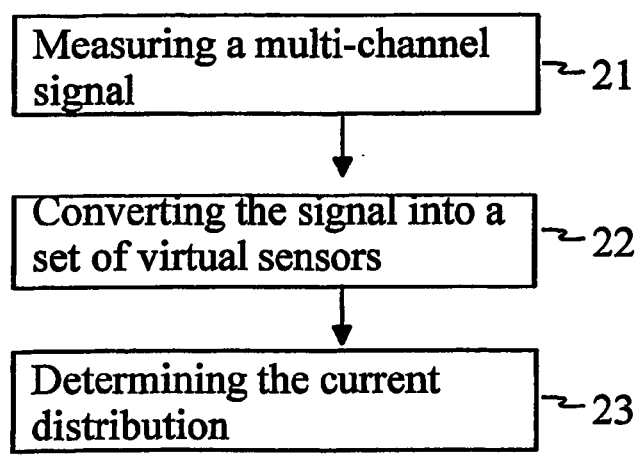

In the following, the invention will be described in detail by means of examples with reference to the accompanying drawing, in which FIG. 1 represents one measurement device in accordance with the present invention; and FIG. 2 is a flow chart illustrating one method in accordance with the present invention.

DETAILED DESCRIPTION OF THE INVENTION

FIG. 1 represents one measurement device in accordance with the present invention comprising a set of measurement channels $1^1, 1^2, \ldots 1^5$ that measure an irrotational and sourceless vector field, in which case at least one measurement sensor $2^1, 2^2, \ldots 2^5$ corresponds to each channel; and processing means 3 for processing the measurement signal. Advantageously, the processing means have been implemented by means of a computer. Further, the processing means include a conversion module 4 for converting a multi-channel measurement signal corresponding to each measurement sensor into the signals of a predetermined set of virtual sensors, and calculation means 5 for determining the current distribution of an object being examined.

Further FIG. 1 shows the object being measured K, into the vicinity of which the measurement sensors $2^1, 2^2, \ldots 2^5$ have been placed. Inside the object being measured there is presented a current loop which describes the source of the magnetic field being measured. The object being measured can be e.g. a human head, and there can be several current sources.

FIG. 2 represents the main steps of one preferred embodiment of the present invention. At first, a set of sensors is used to measure a multi-channel measurement signal, step 21. After that, the signal is converted to correspond to the signal measured using a so-called set of virtual sensors, step 22, making the mathematical operations simpler. Finally, it is possible to simply calculate the current distribution in an object from the signal of the set of virtual sensors, step 23, i.e. in practice, to describe the places and strengths of the current loops inside a sphere or head.

In the following section, the mathematical background and grounds of the invention are described. When the magnetic fields are converted into coefficients $M_{lm} = a_{lm} + ib_{lm}$ associated with the basic solution $r^{-(l+1)} Ylm(\theta, \phi)$ of the Laplace equation, wherein i is an imaginary unit, they can be expressed by means of the current distribution $\vec{J}(\vec{r})$ in spherical coordinates $(r, \theta, \phi)$, whereby they are of the form:

$$M_{lm} = \gamma_l \int_v r^l \vec{X}lm(\theta, \varphi) \cdot \vec{J}(\vec{r}) dv, \quad (1)$$

wherein the integration is performed over the volume being examined, $\gamma_l$ is a constant associated with order l and $\vec{X}lm(\theta,\phi)$ is so-called vector spherical harmonic.

This form can be derived e.g. from publication "Multipole expansions of electromagnetic fields using Debye potentials", C. G. Gray, American Journal of Physics, Vol. 46, pp. 169-179, 1978. The expression mentioned above is of the lead field form, wherein the switching field of the multi-pole coefficient $M_{lm}$ is of the form:

$$\vec{L}_{lm}(\vec{r}) = r^l \vec{X}_{lm}(\theta, \varphi). \quad (2)$$

On the other hand, the vector spherical harmonics form by depth r an orthonormal basis, so with the depth in question, the current distribution can be presented in the function basis in question:

$$\vec{J}(\vec{r}) = \sum_{l=0}^{L} \sum_{m=-l}^{l} c_{lm} f_l(r) \vec{X}_{lm}(\theta, \varphi), \quad (3)$$

wherein f(r) is some radical function.

When as the volume to be examined, spherical volume is selected, by placing the previous expression into the equation (1), the coefficients of the current distribution can be analytically solved:

$$c_{lm} = \hat{\gamma}_l M_{lm} \left[ \int_0^R r^{l+2} f_l(r) dr \right]^{-1}, \quad (4)$$

wherein $\hat{\gamma}_l$ is a constant associated with order l and R is the radius of the sphere to be examined. The previous equation (4) indicates that the coefficients of a current distribution model presented in an orthonormal basis can be solved based on coefficients $M_{lm}$ in a completely trivial manner using analytical expressions without any kind of regularisation. This is computationally very fast and numerically stabile. Function $f_l(r)$ is freely selectable, and can be used to adjust the depth weighing of a current distribution model.

Furthermore, it must be noted that in the case of a spherical conductor, it is possible to use as basis functions also some other orthogonal basis or a basis whose inner products can be otherwise quickly calculated. This is achieved e.g. by slightly breaking the orthogonality in a manner known per se, or by using a basis which is not orthogonal but whose inner products can be calculated beforehand.

The invention is not limited merely to embodiment examples referred to above, instead many variations are possible within the scope of the inventive idea defined by the claims.

What is claimed is:

1. A method for determining a current distribution of an object, the method comprising:
    measuring the magnetic fields in vicinity of the object using a multi-channel measurement device that measures an irrotational and sourceless vector field, whereby one measurement sensor corresponds to each channel;
    converting a multi-channel measurement signal corresponding to each measurement sensor into signals of a predetermined set of virtual sensors, which signals are mutually orthogonal; and
    determining the current distribution of the object being measured from the signals of the set of virtual sensors in a predetermined function basis.

2. The method according to claim 1, wherein the object is approximated using a conductor, and a multi-pole expansion of the field is calculated from the multi-channel measurement signal.

3. The method according to claim 2, wherein the multi-pole expansion is calculated by taking into account magnetic fields emitted by sources outside the object.

4. The method according to claim 2, wherein the multi-pole expansion is calculated by ignoring magnetic fields emitted by sources outside the object.

5. The method according to claim 4, wherein:
    an orthonormal function basis is placed into a current distribution equation; and coefficients of the current distribution are analytically solved from the equation:

$$c_{lm} = \hat{\gamma}_l M_{lm} \left[ \int_0^R r^{l+2} f_l(r) dr \right]^{-1},$$

wherein $c_{lm}$ are said coefficients, $\hat{\gamma}_l$ is a constant associated with order l, $M_{lm}$ are multi-pole coefficients, R is a radius of a sphere to be examined, r is the radial distance as a variable and $f_l(r)$ is a selectable radial function.

6. The method according to claim 2, wherein external interferences are eliminated prior to the step of converting.

7. The method according to claim 2, wherein as an orthonormal function basis, a current distribution equation of the following form is selected:

$$\vec{J}(\vec{r}) = \sum_{l=0}^{L} \sum_{m=-l}^{l} c_{lm} f_l(r) \vec{X}_{lm}(\theta, \varphi),$$

wherein $\vec{J}(\vec{r})$ is the current distribution, L and l are orders, $C_{lm}$ are coefficients of the current distribution, $f_l(r)$ is a selectable radial function and $\vec{X}_{lm}(\theta,\phi)$ is vector spherical harmonic.

8. The method according to claim 7, wherein function $f_l(r)$ is used to adjust a depth weighing of a current distribution model.

9. The method according to claim 1, wherein the object is approximated using a spherically symmetric conductor.

10. A measurement device for determining a current distribution of an object by measuring magnetic fields in a vicinity of the object, the measurement device comprising:
    a set of measurement channels ($1, 1^1, 1^2, \ldots 1^n$) that measure an irrotational and sourceless vector field, in which case at least one measurement sensor $2, 2^1, 2^n, \ldots 2^n$) corresponds to each channel;
    processing means for processing a measurement signal in which the object is approximated using a spherical-symmetrical conductor, wherein
    the processing means include a conversion module for converting a multi-channel measurement signal corresponding to each measurement sensor into signals of a predetermined set of virtual sensors, which signals are mutually orthogonal; and
    calculation means for determining the current distribution of an object being examined from the set of virtual sensors using depth r in a predetermined orthonormal function basis.

11. The measurement device according to claim 10, wherein the calculation means are arranged to calculate a multi-pole expansion from the multi-channel measurement signal.

12. The measurement device according to claim 11, wherein the multi-pole expansion is calculated by taking into account magnetic fields emitted by sources outside the object being measured.

13. The measurement device according to claim 11, wherein the multi-pole expansion is calculated by ignoring magnetic fields emitted by sources outside the object being measured.

14. The measurement device according to claim 13, wherein
   the orthonormal function basis is placed into the current distribution equation; and
   coefficients of the current distribution are solved analytically from the equation:

$$c_{lm} = \hat{\gamma}_l M_{lm} \left[ \int_0^R r^{l+2} f_l(r) dr \right]^{-1},$$

wherein $c_{lm}$ are said coefficients, $\gamma_l$ is a constant associated with order l, $M_{lm}$ are multi-pole coefficients, R is a radius of a sphere to be examined, r is the radial distance as a variable and $f_l$ is a radial function to be selected.

15. The measurement device according to claim 11, wherein as the orthonormal function basis, a current distribution equation with the following form is selected:

$$\vec{J}(\vec{r}) = \sum_{l=0}^{L} \sum_{m=-l}^{l} c_{lm} f_l(r) \vec{X}_{lm}(\theta, \varphi),$$

wherein $\vec{J}(\vec{r})$ is the current distribution, L and l, are orders, $c_{lm}$ are coefficients of the current distribution, $f_l(r)$ is a radial function to be selected and $\overline{X}_{lm}(\theta,\phi)$ is vector spherical harmonic.

16. The measurement device according to claim 15, wherein $f_l(r)$ is used to adjust a depth weighing of a current distribution model.

17. The measurement device according to claim 10, wherein the measurement device converts the signals into a set of virtual sensors prior to storage, and analysis software converts the stored data into a current distribution.

* * * * *